(12) United States Patent
Stadler et al.

(10) Patent No.: US 10,780,191 B2
(45) Date of Patent: Sep. 22, 2020

(54) STERILIZER

(71) Applicant: BELIMED AG, Zug (CH)

(72) Inventors: Hans Stadler, Sulgen (CH); Daniel Düring, Niederbueren (CH)

(73) Assignee: BELIMED AG, Zug (CH)

( * ) Notice: Subject to any disclaimer, the term of this patent is extended or adjusted under 35 U.S.C. 154(b) by 392 days.

(21) Appl. No.: 15/550,065

(22) PCT Filed: Feb. 8, 2016

(86) PCT No.: PCT/EP2016/052623
§ 371 (c)(1),
(2) Date: Aug. 10, 2017

(87) PCT Pub. No.: WO2016/128351
PCT Pub. Date: Aug. 18, 2016

(65) Prior Publication Data
US 2018/0028704 A1    Feb. 1, 2018

(30) Foreign Application Priority Data

Feb. 12, 2015   (EP) .................................... 15154796

(51) Int. Cl.
*A61L 2/28*     (2006.01)
*A61L 2/07*     (2006.01)
(Continued)

(52) U.S. Cl.
CPC .................................... *A61L 2/28* (2013.01); *A61L 2/07* (2013.01); *F28D 15/00* (2013.01); *F28F 23/00* (2013.01); *A61L 2202/14* (2013.01)

(58) Field of Classification Search
CPC ... A61L 2/07; A61L 2/28; F28D 15/00; F28D 23/00
See application file for complete search history.

(56) References Cited

U.S. PATENT DOCUMENTS 3,245,461 A    4/1966  Allington
5,565,634 A *  10/1996 Graessle .................... A61L 2/28
                                                   422/119

(Continued)

FOREIGN PATENT DOCUMENTS

DE   10 201 001 6017 A1   11/2011
EP      0 982 039 A1       3/2000
(Continued)

OTHER PUBLICATIONS

Written Opinion filed in corresponding PCT Application No. PCT/EP2016/052623 dated Apr. 15, 2016.
(Continued)

*Primary Examiner* — Sean E Conley
(74) *Attorney, Agent, or Firm* — Davis & Bujold PLLC; Michael J. Bujold

(57) ABSTRACT

A sterilizer comprises a sterilization chamber (1) with a test device (2) for testing the effectiveness of a sterilization process. The test device (2), in turn, comprises a test element (3) with a sensor (4) for measuring at least one parameter, and cooling mechanism (5) for cooling the test element (3). The test device (2), as a whole, is completely accommodated within the interior (8) of the sterilization chamber (1).

18 Claims, 4 Drawing Sheets

(51) Int. Cl.
F28D 15/00 (2006.01)
F28F 23/00 (2006.01)

(56) References Cited

U.S. PATENT DOCUMENTS

| | | |
|---|---|---|
| 7,153,470 B2 | 12/2006 | Stockard |
| 2007/0240578 A1 | 10/2007 | DiLeo |
| 2007/0274858 A1 | 11/2007 | Childers et al. |

FOREIGN PATENT DOCUMENTS

| | | |
|---|---|---|
| EP | 1 342 478 A1 | 10/2003 |
| EP | 1 844 838 A2 | 10/2007 |
| EP | 2 366 411 A1 | 9/2011 |
| WO | 00/06211 A1 | 2/2000 |
| WO | 2012/135694 A2 | 10/2012 |

OTHER PUBLICATIONS

International Search Report filed in corresponding PCT Application No. PCT/EP2016/052623 dated Apr. 15, 2016.

\* cited by examiner

STERILIZER

The present invention relates to a sterilizer according to the preamble of claim 1.

Sterilizers, in particular steam sterilizers, are used in a clinical setting and in related fields in order to ensure the substantial sterility of sterile materials. Sterile materials are generally medical instruments or the work clothing of personnel who work under sterile conditions.

In order to ensure the requisite sterility in routine operation, the effectiveness of a sterilization process has to be checked at regular intervals. This checking normally takes place indirectly by means of a test device which is exposed to the sterilization conditions.

In the medical field, steam sterilizers with a prevacuum are widespread. In such sterilizers, the sterilization is carried out in a sterilizer chamber. The method employed here involves essentially three phases. In a first phase, known as the venting phase, also referred to as the pretreatment phase, the sterilizer chamber is evacuated and the air contained therein replaced with steam. This process can be repeated several times. The expression fractionated prevacuum is then also used. In the second phase, the actual sterilization takes place, wherein the steam acts on the sterile materials in the sterilizer chamber for a particular time under a given pressure and temperature. The third phase involves drying, in which condensate in the interior of the sterilizer chamber is removed by vacuum and heating.

In medical steam sterilizers with fractionated prevacuum, routine performance checking using what is known as the Bowie-Dick test is prescribed. This test simulates the poor steam penetration of a tightly compact package of 7 kg of textiles. According to standard ISO 11140-4 for packaged sterile materials and porous loads, such proof is obligatory. It also serves to prove the conformity with standard EN 285 and should be carried out once a day as a routine test according to ISO 17665-1 in order to check the function of the prevacuum. One possible test arrangement for the Bowie-Dick test comprises a stack of tightly compressed absorbent paper into which a test card has been inserted. Applied to the test card are chemical indicators which indicate the sterilization action by a change in color.

However, chemical indicators can also be inserted into a gas-permeable test container and be exposed to the sterilization conditions. If, before the introduction of the steam, the air is not sufficiently removed from the sterilizer, the steam saturation in the test container does not reach the necessary concentration, with the result that the deficient function of the sterilizer is rendered visible by the indicators. In addition to chemical indicators, it is also possible for electronic sensors to be used in the Bowie-Dick test. Thus, it is possible, for example, for a test element consisting of a system of cavities with one or more temperature sensors to be exposed to the sterilization conditions. By way of one or more temperature measurements taken at the test element, it is possible to decide whether a sterilization process has been successful.

DE 10 2010 016017 A1 describes a sterilizer having a sterilizer chamber and a test device for testing the effectiveness of the sterilization process. Said test device comprises a test element and a probe, wherein the probe is fitted in the test element. The test device is in that case designed such that the test element is arranged outside and the probe at least partially inside the sterilizer chamber. Furthermore, the test device is generally firmly connected to the sterilizer chamber. However, such an apparatus has the drawback that condensate that accumulates in the test element can be removed only very slowly via evaporation. In addition, the described design is comparatively bulky on account of the presence of components outside the sterilizer chamber.

The object of the invention is to overcome the drawbacks of the prior art.

In particular, the object of the present invention is to create a sterilizer having a sterilizer chamber and having a test device for testing the effectiveness of a sterilization process, which is reliable in operation and is easy to handle. The sterilizer should moreover be usable in a versatile manner and configured in a structurally simple manner. It should have a compact design, and be cost-effective to produce. Furthermore, low-maintenance operation should be possible.

These objects are achieved by a sterilizer which has the features of claim 1.

The invention relates to a sterilizer having a sterilizer chamber and having a test device for testing the effectiveness of a sterilization process. Such testing can include the testing of the effectiveness of successful venting during the sterilization process, as is prescribed in standard EN 285 for a Bowie-Dick test. The test device comprises a test element having a sensor for measuring at least one parameter and a cooling means for cooling the test element. The invention is characterized in that the entire test device is arranged completely in the interior of the sterilizer chamber.

The expression "cooling means for cooling the test element" should be understood in the present context as meaning means with which heat transfer from the test element to some other medium can be achieved.

As a result of this arrangement of the test device, it is possible, without any further design measures, to heat the test device in the third phase of the sterilization process in a controlled manner under vacuum, with the result that condensate that arises can be evaporated more easily. In this content, condensate is understood as meaning sterilization agent which has accumulated in liquid form within the sterilizer chamber during the sterilization process. In conventional steam sterilizers, it is typically condensed water vapor.

Furthermore, the arrangement of the test device in the interior of the test chamber results in a more compact design of the entire sterilizer. In addition, as a result of the direct presence of the test device in the interior of the sterilizer chamber, very direct measurement of the effectiveness of the sterilization process is possible. The evaluation of the test results can take place efficiently and with advantageous convenience, since the test device is arranged fixedly in the sterilizer chamber and does not have to be removed for this purpose.

The test device may additionally comprise a probe, which is attached to the test element. This probe can be in the form of a hollow body for conducting sterilization agent, in particular water vapor and/or other gases. This hollow body can be in the form of a pipe consisting of plastic and/or metal and be open at the end away from the test element, in order to conduct sterilization agent and/or heat to the test element. Such a probe can be configured, for example by being coiled multiple times, such that the test device is suitable for testing the effectiveness of the sterilization process for medical instruments which, on account of their geometry or other properties, represent a particular challenge for the sterilization process.

The test element may be embodied as a, preferably cylindrical, capsule with an interior. This represents a prefer red geometry of the test element, which is easy to manufacture and has particularly favorable testing properties.

The interior of the capsule may be in fluidic communication with the sterilizer chamber directly or indirectly via the probe. In such an embodiment, in the first phase of the sterilization process, the air located in the test element is exchanged for the sterilization agent (for example water vapor) by the applied prevacuum via the probe. As a result, depending on the sterilization agent, in particular heating of the cooled test element occurs. If the effectiveness of the sterilization process were reduced by the presence of residual air within the sterilizer chamber, for example because of a leak, a temperature deviation from an "ideal" process would be detectable within the test element. This temperature deviation can also be expressed, inter alia, as a time delay until a particular temperature within the test element is reached.

The sensor and the probe may be attached to or arranged at different ends of the capsule, in particular on the end face. As a result of this arrangement of the probe and sensor, particularly sensitive testing can b achieved.

The sensor may, in order to measure a parameter, be selected from a list consisting of temperature, pressure and humidity. These variables allow clear conclusions to be drawn about the effectiveness of a sterilization process. In addition, a large number of sensors of a wide variety of specifications are commercially available for these parameters.

The sterilizer chamber may be subdivided into a loading area and a testing area. The testing area may preferably be arranged beneath or to the side of the loading area. This arrangement has the advantage that the testing area extends over the coldest region of the sterilizer chamber next to the outlet thereof. However, in some cases, it is also advantageous for the loading area to be arranged beneath or to the side of the testing area. In both cases, the test device is preferably arranged in the testing area.

The cooling means for cooling the test element may comprise a heat transfer section for passing through a coolant or a refrigerant, in particular a cooling jacket or a cooling coil. As a result of such active cooling of the test element, particularly efficient control of the temperature thereof can be achieved.

The cooling means for cooling the test element may additionally comprise a supply line for supplying the coolant or the refrigerant into the sterilizer chamber and a drain line for draining the coolant or the refrigerant out of the sterilizer chamber. However, it is also possible for a supply line for supplying the coolant or the refrigerant into the sterilizer chamber and a drain line for draining the coolant or the refrigerant out of the sterilizer chamber to be attached to the cooling means for cooling the test element. These embodiments allow particularly efficient heat dissipation out of the sterilizer chamber.

The coolant or the refrigerant may be able to be circulated in a circuit. This circuit can be arranged completely in the sterilizer. As a result, it is possible to operate a sterilizer according to the invention independently of further infrastructure such as a cooling water supply, for example.

In a sterilizer with a coolant, the coolant may be composed of a pure substance or a mixture of substances, wherein at least one precursor substance of the coolant is selected from a list consisting of water, ethylene glycol, methanol, ethanol, propanol, isopropanol, acetone, air and thermal oil. Mixtures of these coolants are distinguished inter alia by a particularly low melting point, good fluidmatic properties and good corrosion behavior.

In a sterilizer with a refrigerant, the refrigerant may be composed of a pure substance or a mixture of substances, wherein at least one precursor substance of the refrigerant is selected from a list consisting of ammonia, carbon dioxide, water, a hydrocarbon, an HCFC, an HFC, a CFC and a PFC. These are refrigerants that have been used for many years, which are usable in combination with a wide selection of refrigerating machines.

A signal, preferably an electrical signal, generated by the sensor may be able to be passed out of the sterilizer chamber via a cable connection. Such a cable connection represents a reliable and cost-effective connection of the sensor. In addition to an electrical signal, it is also possible to pass a value measured by the sensor out of the sterilizer chamber by way of an optical signal, preferably via an optical fiber.

However, a signal, preferably an electrical signal, generated by the sensor may also be able to be passed out of the sterilizer chamber via a radio connection, comprising a transmitter and a receiver. A radio connection has the advantage that no lines have to be passed through a wall of the sterilizer chamber. This dispenses with possible sealing problems. Furthermore, sensors can be exchanged more easily in this way, thereby simplifying variable instrumentation of the sterilizer chamber.

However, a signal, preferably an electrical signal, generated by the sensor may also be able to be passed out of the sterilizer chamber inductively, in particular by means of two inductively coupled coils. In this context, inductively is understood as meaning that the connection of the signal from the interior of the sterilizer chamber to the exterior of the sterilizer chamber is realized by two coils which are inductively coupled. An inductive connection has the advantage that, in contrast to a cable connection, it does not require an aperture in a wall of the sterilizer chamber, and moreover, in comparison with a radio connection, is less susceptible to interference.

All of these configurations, in which a signal generated by the sensor is able to be passed out of the sterilizer chamber via a cable connection, have the advantage that the evaluation can take place during an ongoing sterilization process, with the result that a time saving is achievable.

Furthermore, a signal, preferably an electrical signal, generated by the sensor can also be recorded by a data storage unit, for example a data logger, located in the sterilizer chamber.

The test device may be inserted at least partially into a connector, in particular a validation connector, attached to the sterilizer chamber. It goes without saying here that the interior of the connector is also part of the sterilizer chamber. This attachment of the test device has the advantage that existing sterilizers can easily be retrofitted according to the invention. This is particularly advantageous with regard to existing systems since the test device is usable not only for the Bowie-Dick test, carried out as an empty test, but also as an air detection device or in conjunction with a batch control system.

In the present context, an air detection device is understood as being an apparatus which, in the first phase of the sterilization process, known as the venting phase, also referred to as the pretreatment phase, with the steam sterilizer partially or fully loaded, is used in order to check the correct replacement of the air contained in the sterilizer chamber with wafer vapor.

In the present context, a batch control system, is understood as being a system which, in the second phase of the sterilization process, the actual sterilization phase, with the steam sterilizer partially or fully loaded, records physical parameters which allow conclusions to be drawn about the effectiveness of the sterilization process.

With such fitting of the test device within the sterilizer chamber, the probe may project out of the connector into a testing areas within the sterilizer chamber. This makes it possible for the test nevertheless to take place in the coldest area of the sterilizer chamber.

The test device may be held in a stable position in the connector and thus in the sterilizer chamber via a cover place that closes off the connector. As a result, conceivably easy mounting of so test device within the sterilizer chamber can be achieved.

The cover plate may be able to be attached to the connector via a quick-release fastener. Said quick-release fastener is preferably a flange clamp that acts on a flange that terminates the connector and on the cover plate. However, other variants of a quick-release fastener, for example a bayonet fastener, a screw fastener or a lever fastener, would also be conceivable. As a result of a quick-release fastener being used, the test device can be inserted into the sterilizer chamber in a particularly time-efficient and user-friendly manner, thereby making in particular maintenance work or validation measurements on she sterilizer much easier.

Further advantages and individual features of the invention can be gathered from the following description of an exemplary embodiment and from the drawings, in which, schematically:

Figure 1:
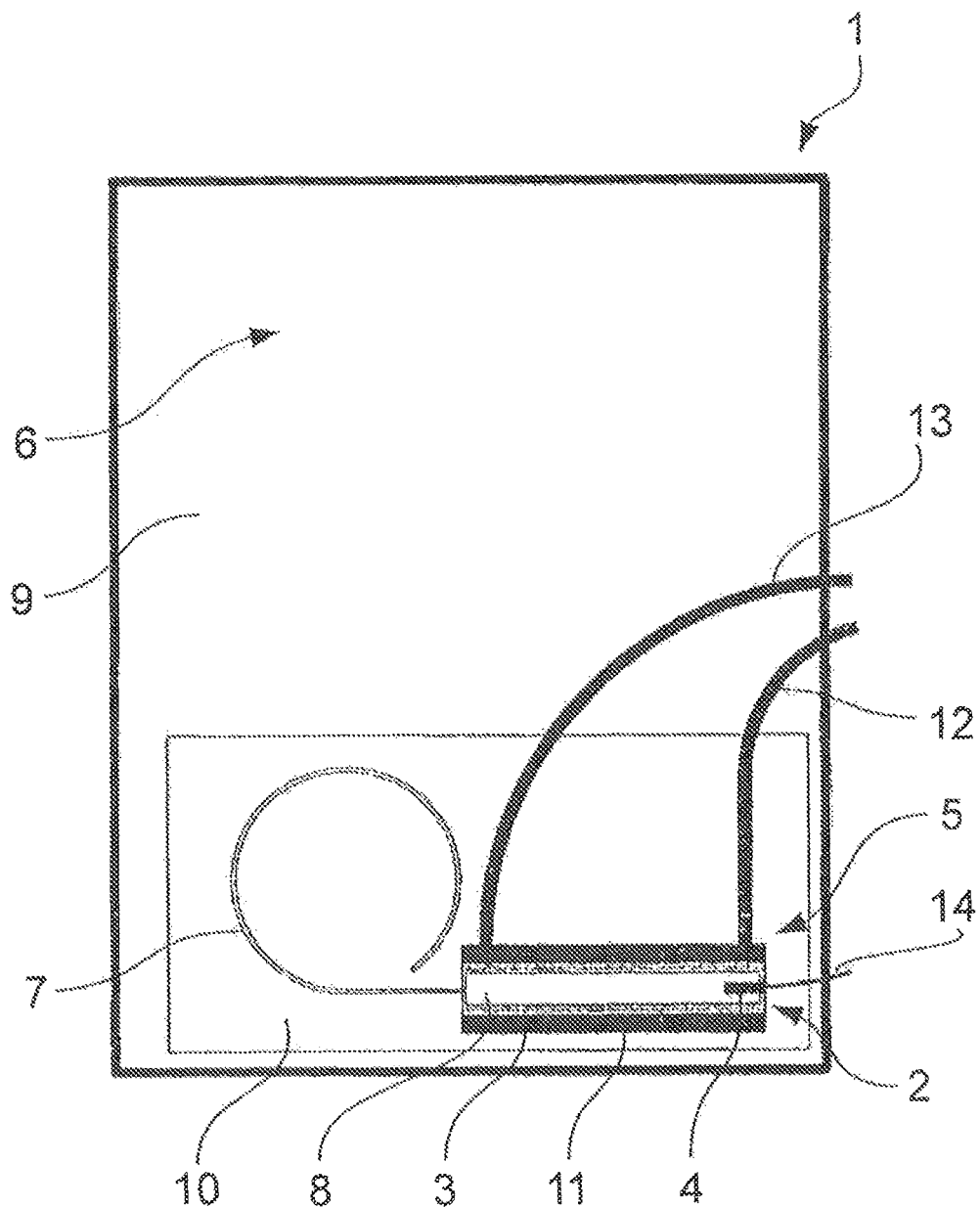
FIG. 1 shows an illustration of the sterilizer chamber of a sterilizer according to the invention.

FIG. 1 shows a schematic illustration of the sterilizer chamber 1 of a sterilizer according to the invention. The interior 6 of the sterilizer chamber 1 is subdivided into a loading area 9 and a testing area 10. While the loading area 9 is intended to be loaded with material to be sterilized, a test device 2 for testing the effectiveness of a sterilization process is arranged in the testing area 10. The test device 2 comprises a test element 3 in the form of a cylindrical capsule and a probe 7, which is in the form of an elongate cavity. The interior 8 of the capsule 3 in this case is in fluidic communication with the sterilizer chamber via the probe 7. Arranged in the interior 8 of the capsule 3 is a sensor 4, in the present case a temperature sensor. The sensor 1 is connected to the exterior of the sterilizer chamber 1 via a cable connection 14. The test device furthermore has a cooling means 1 for cooling the test element 3. In this case, the test element 3 emits energy in the form of heat to the cooling means 5 via a heat transfer section 11. In the present case, the cooling means 5 comprises a cooling jacket which envelops the test element 3 in the form of a capsule. The cooling jacket is supplied with a coolant via a supply line 12 from the exterior of the sterilizer chamber 1. In a corresponding manner, a drain line 13 for draining the coolant out of the sterilizer chamber is also provided.

Figure 2:
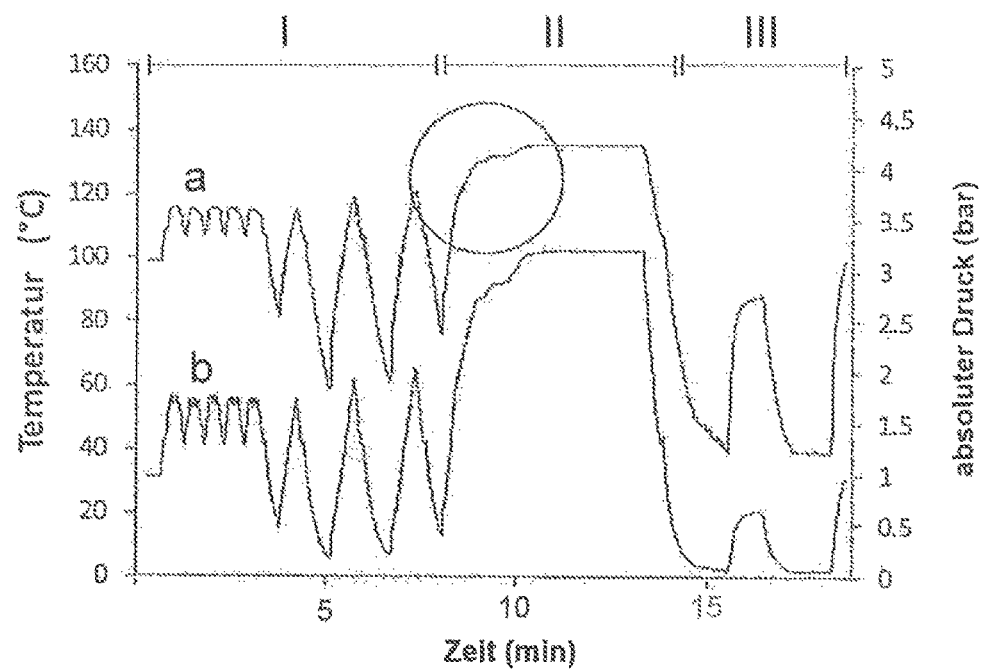
FIG. 2 shows the time curve of the temperature and absolute pressure, measured by a testing device of a sterilizer according to the invention, within the sterilizer chamber over a typical sterilization process.
Figure 3:
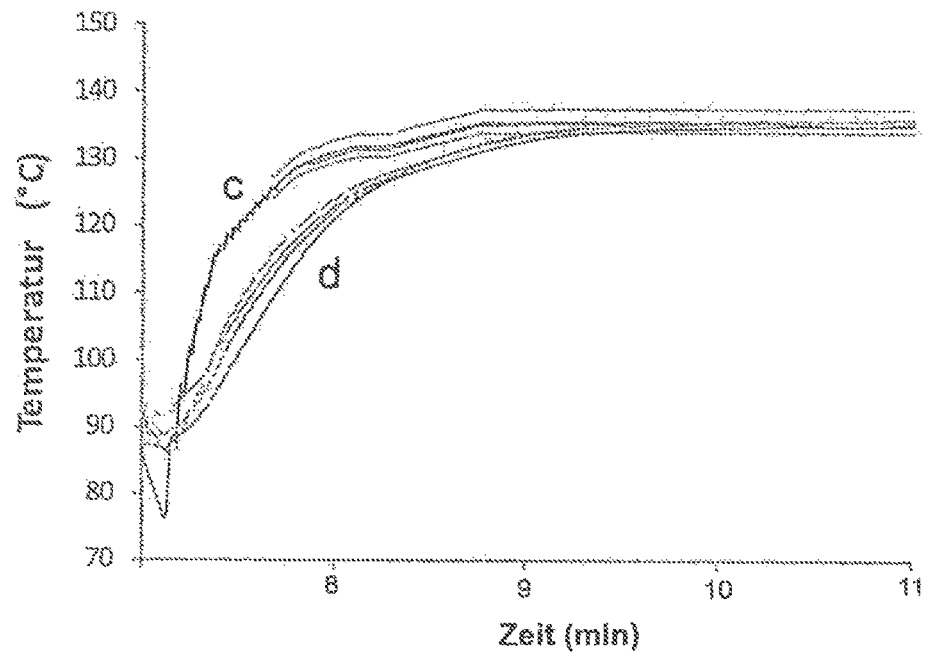
FIG. 3 shows a partial enlargement of the area indicated by a circle in FIG. 2.

In FIGS. 2 and 3, a method for testing the effectiveness of the sterilization process of a steam sterilizer according to the invention is explained by way of example. In the case shown, the sterilizer operates under what are known as saturated steam conditions. Saturated steam is understood in this context as meaning water, the liquid and gaseous phases of which are present simultaneously in thermodynamic equilibrium. Under saturated steam conditions, temperature and pressure are mutually dependent variables which are described by what is known as the saturated steam curve. The profile of this curve depends on the substance amount fraction of water in the present system. This effect can be used to ascertain whether there is residual air within the sterilizer chamber.

Curve a in FIG. 2 reproduces the course of the absolute pressure within the sterilizer chamber as a function of time over the sterilization process. Curve b represents, in a corresponding manner, the temperature measured by the probe 4 in the interior of the test element 8. It can be seen that, in a first phase (I) of the sterilization process, the air within the sterilization chamber 1 is displaced entirely by wafer vapor over a series of different cycles consisting of evacuation and filling with steam. After this first phase, in a second phase (II), the actual sterilization process takes place, in which the sterilizer chamber is filled with saturated steam and is kept at a defined temperature. In the third phase (III), vacuum is again applied multiple times and the interior of the sterilizer chamber 1 is dried by simultaneously increasing the temperature, with the result that condensation water that has arisen is removed. In said third phase (III), it is also possible for vacuum to be applied only once, however.

FIG. 3 illustrates the area indicated by a circle in FIG. 2 in an enlarged manner. The set of curves c in this case shows the typical temperature profile under saturated steam conditions at a substance amount fraction of water within the sterilizer chamber which corresponds to the required specifications. By contrast, the set of curves d shows the temperature profile under saturated steam conditions with an insufficient substance amount fraction of water within the sterilizer chamber, for example on account of the presence of residual gas. It can clearly be seen from the different curve pretties that the fractionated prevacuum in the case of set of curves d did not meet the requirements and the sterilization process thus did not have the desired effectiveness.

In a sterilizer of this kind, the measured temperature profile can be evaluated automatically, wherein an ongoing sterilization process is stepped in the event of deviations of the measured values from the specifications. Possible conditions for this are, for example, that the measured temperature deviates from the theoretical value by no more than 10%, preferably 5%, more preferably 2%. In accordance with standard EN 11140-1, an alternative condition can be that the temperature deviation is at most 1° C. at the start of phase (II) (known as the holding time).

The measured temperature profiles can be routinely recorded for quality assurance and stored in a database, for example of what is known as a batch control system.

Figure 4:
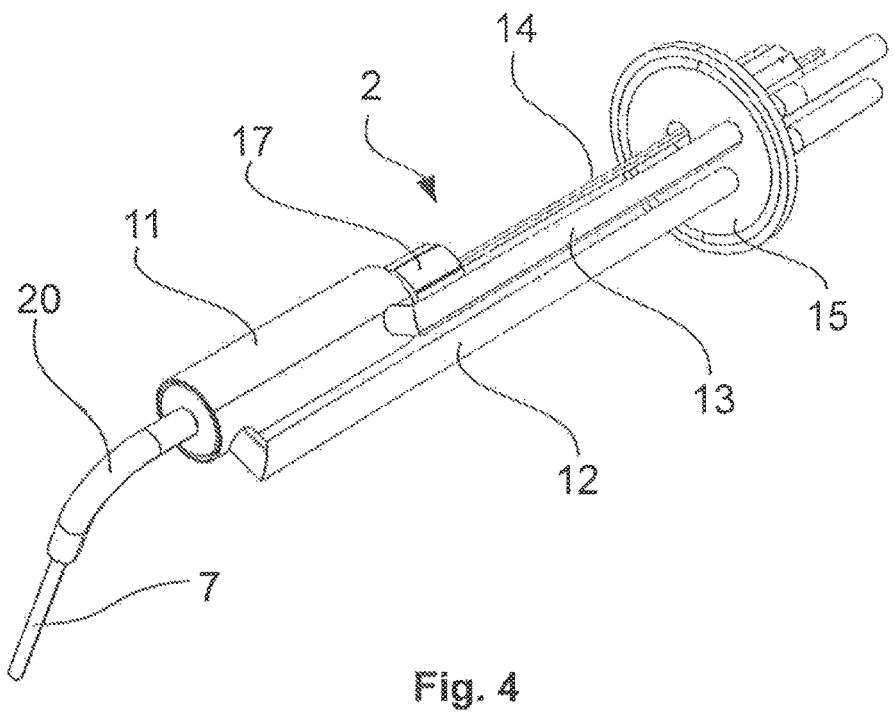
FIG. 4 shows a perspective illustration of a test device for a sterilizer according to the invention.

FIG. 4 shows a preferred exemplary embodiment of a test device 2 for a sterilizer according to the invention. In said example, the test element 3 is completely surrounded by the heat transfer section 11, which is embodied as a cooling jacket here. The supply of coolant takes place via the supply line 12, while it is drained via the drain line 13. The supply line 12 and drain line 13 are embodied here as stainless steel pipes which are passed through the cover plate 15. The cooling means shown is designed for air as coolant. Furthermore, a cable connection 14 is likewise passed through the cover plate 15, said cable connection 14 connecting a sensor 4 in the interior of the test element 3 (not visible here) to the exterior of the sterilizer chamber 1. It is apparent that the supply line 12, the drain line 13 and the cable connection 14 are guided in a substantially parallel manner. Attached to the opposite end of the test body 3 from the cover plate 15 is a probe 7 that is curved at a right angle.

Figure 5:
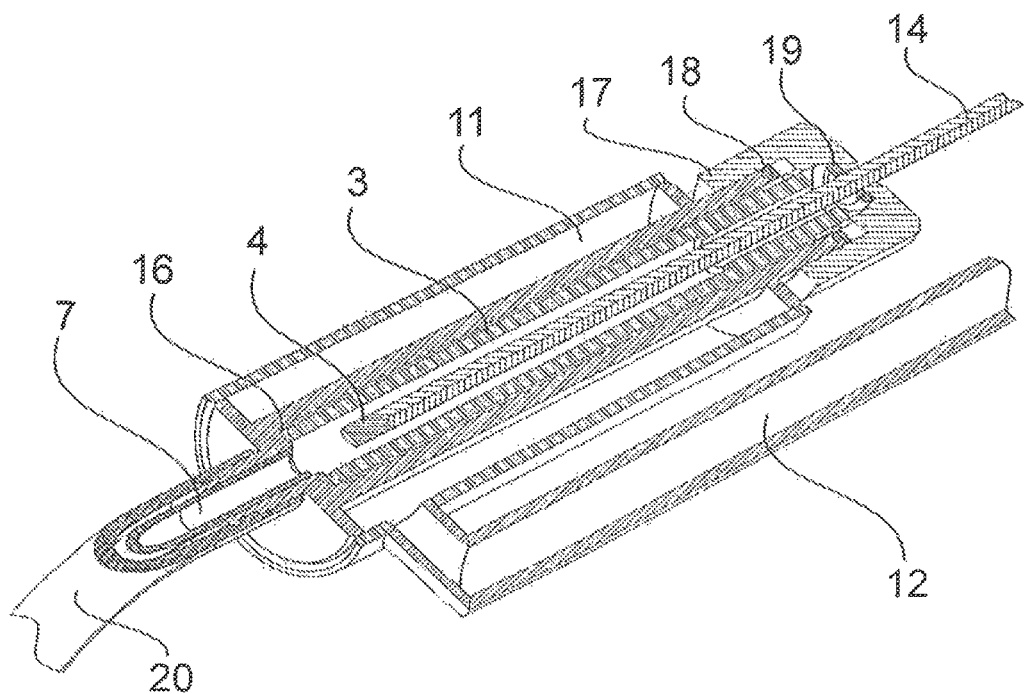
FIG. 5 shows a partial enlargement of the illustration according to FIG. 4 as a sectional view.

FIG. 5 reveals further details of the test element 3 and the cooling jacket 11. Thus, the sensor 4 arranged in the test element 3, in this case a temperature-sensor, can be seen. The test element 3 is a substantially cylindrical capsule which is manufactured from a ceramic material. The cooling jacket 11 forms a likewise cylindrical receptacle 16, into which the test element 3 is inserted. The receptacle 16 is closed off by a cover 17, through which the cable connection 14 is passed. In order to ensure a sealed closure of the receptacle 16, seals 18 and 19 are attached to the cover 17. At its opposite end from the cover 17, the test element 3 is connected to the probe 17. The probe 17 is, to this end, plugged into the receptacle 15 and is in contact at the end face with the test element 3. The probe 7 is secured to the cooling jacket 11 by the sleeve element 20.

Figure 6:
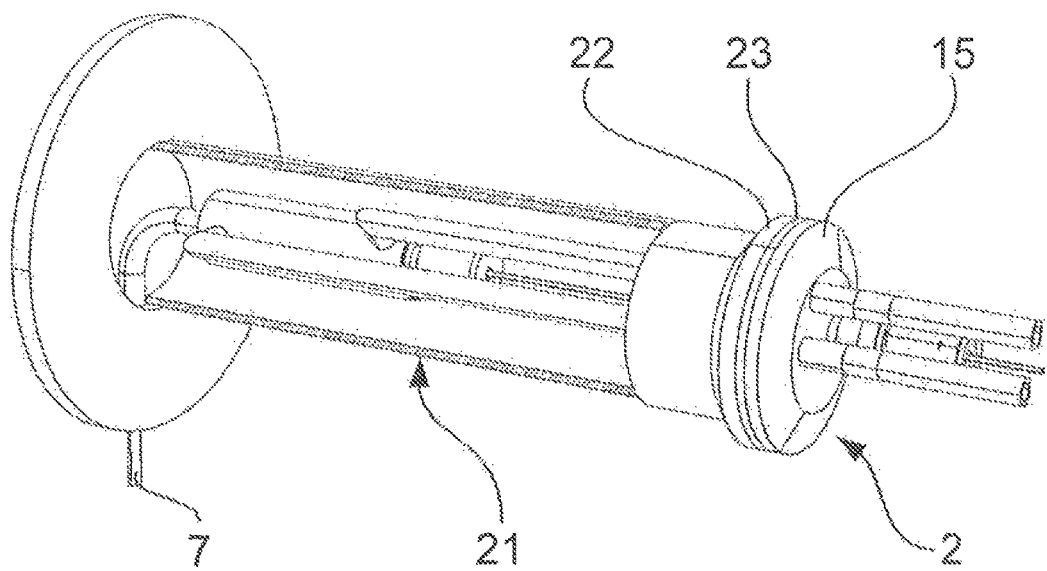
FIG. 6 shows a perspective illustration of a test device according to FIGS. 4 and 5, used in a validation connector of a sterilizer chamber.

In the illustration according to FIG. 6, the above-described test device 2 has been inserted into a validation connector 21 of a sterilizer chamber 1. In this case, the connector 21 is shown in longitudinal section such that the test device 2 is visible. The validation connector 21 has, at its end away from the sterilization chamber 1, a flange 22, against which the cover plate 15 bears with a precise fit. Fitted between the flange 22 and the cover plate 15 is a sealing element 23. The test device 2 is held in a stable position in the interior of the validation connector 21, wherein the probe 7 projects into a testing area in the interior of the sterilizer chamber 1.

Figure 7:
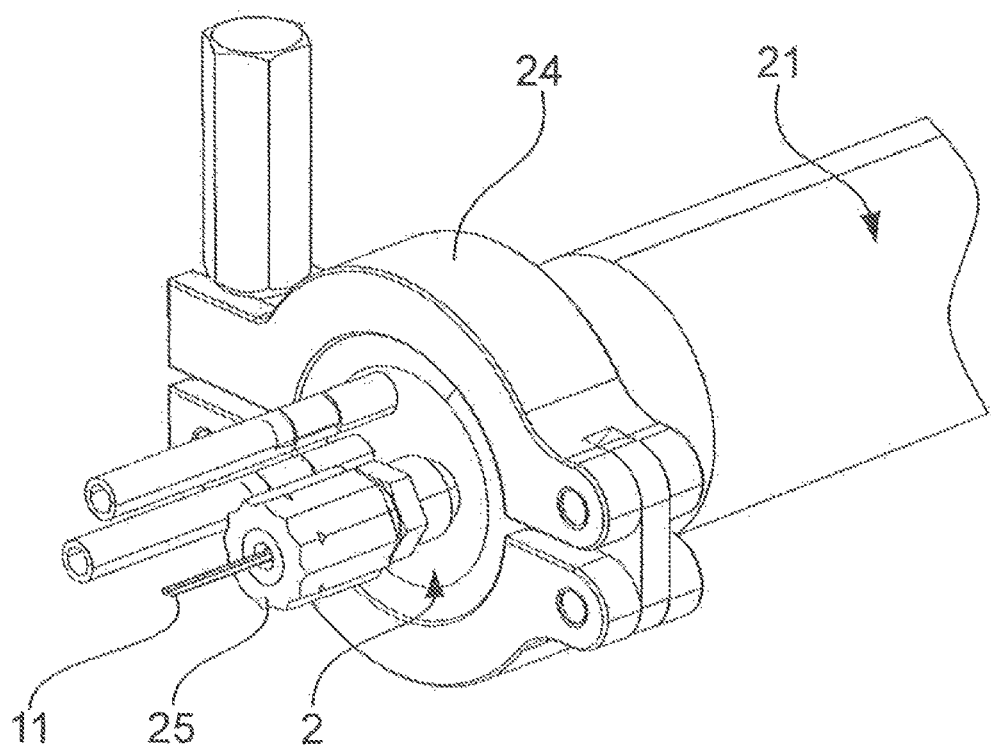
FIG. 7 shows a further perspective illustration of a test device according to FIGS. 4 to 6 used in a validation connector of a sterilizer chamber.

FIG. 7 shows a validation connector 21, provided with the described test device 2, from a different perspective than FIG. 6. The test device 2 is secured to the connector 21 via a flange clamp 24. In addition, a cover 25 is clearly visible, through which the cable connection 14 is passed out of the sterilizer chamber 1.

The invention claimed is:

1. A sterilizer having:
   a sterilizer chamber, and
   a test device for testing the effectiveness of a sterilization process,
   wherein the test device comprises a test element having a sensor for measuring at least one parameter,
   a cooling means for cooling the test element, and the test device is arranged entirely and completely within an interior of the sterilizer chamber, wherein the cooling means for cooling the test element comprises a heat transfer section for passing through a coolant or a refrigerant, and wherein the cooling means for cooling the test element additionally comprises a supply line for supplying the coolant or the refrigerant into the sterilizer chamber and a drain line for draining the coolant or the refrigerant out of the sterilizer chamber.

2. The sterilizer as claimed in claim 1, wherein the test device additionally comprises a probe which is attached to the test element.

3. The sterilizer as claimed in either of claim 1, wherein the test element is embodied as a capsule with an interior.

4. The sterilizer as claimed in claim 2, wherein the test element is embodied as a capsule with an interior, and the interior of the capsule is in directly or indirectly fluidic communication with the sterilizer chamber via the probe.

5. The sterilizer as claimed in claim 4, wherein the sensor and the probe are attached to or arranged at different ends of the capsule.

6. The sterilizer as claimed in claim 1, wherein the sensor is suitable for measuring a parameter selected from a list consisting of temperature, pressure and humidity.

7. The sterilizer as claimed in claim 1, wherein the sterilizer chamber is subdivided into a loading area and a testing area, and the test device is arranged in the testing area.

8. The sterilizer as claimed in claim 1, wherein a supply line for supplying the coolant or the refrigerant into the sterilizer chamber and a drain line for draining the coolant or the refrigerant out of the sterilizer chamber is attached to the cooling means for cooling the test element.

9. The sterilizer as claimed in claim 1, wherein that the coolant or the refrigerant is able to be circulated in a circuit.

10. The sterilizer as claimed in claim 1 with a coolant, wherein the coolant comprises a pure substance or a mixture of substances, and at least one precursor substance of the coolant is selected from a group consisting of water, ethylene glycol, methanol, ethanol, propanol, isopropanol, acetone, air and thermal oil.

11. The sterilizer as claimed in claim 1, wherein the refrigerant comprises a pure substance or a mixture of substances, and at least one precursor substance of the refrigerant is selected from a group consisting of ammonia, carbon dioxide, water, a hydrocarbon, an HCFC, an HFC, a CFC and a PFC.

12. The sterilizer as claimed in claim 1, wherein a signal generated by the sensor is able to be passed out of the sterilizer chamber via a cable connection.

13. The sterilizer as claimed in claim 1, wherein a signal generated by the sensor is able to be passed out of the sterilizer chamber via a radio connection comprising a transmitter and a receiver.

14. The sterilizer as claimed in claim 1, wherein a signal generated by the sensor is able to be inductively passed out of the sterilizer chamber.

15. The sterilizer as claimed claim 1, wherein the test device is inserted at least partially into a connector attached to the sterilizer chamber.

16. The sterilizer as claimed in claim 15, wherein the probe projects out of the connector into a testing area within the sterilizer chamber.

17. The sterilizer as claimed in claim 15, wherein the test device is held in a stable position in the connector, and thus in the sterilizer chamber, via a cover plate that closes off the connector.

18. The sterilizer as claimed in claim 17, wherein the cover plate is attachable to the connector via a quick-release fastener.

* * * * *